US008723532B2

(12) United States Patent
Asjes et al.

(10) Patent No.: US 8,723,532 B2
(45) Date of Patent: May 13, 2014

(54) CAPACITIVE PROXIMITY DEVICE AND ELECTRONIC DEVICE COMPRISING THE CAPACITIVE PROXIMITY DEVICE

(75) Inventors: Ronald Jan Asjes, Eindhoven (NL); Adrianus Petrus Johanna Maria Rommers, Eindhoven (NL); Henricus Antonius Verspaget, Eindhoven (NL); Cristian Presura, Eindhoven (NL); Antonius Hermanus Maria Blom, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 588 days.

(21) Appl. No.: 12/995,202

(22) PCT Filed: Jun. 10, 2009

(86) PCT No.: PCT/IB2009/052469
§ 371 (c)(1),
(2), (4) Date: Nov. 30, 2010

(87) PCT Pub. No.: WO2009/150618
PCT Pub. Date: Dec. 17, 2009

(65) Prior Publication Data
US 2011/0084709 A1    Apr. 14, 2011

(30) Foreign Application Priority Data

Jun. 13, 2008 (EP) .................................... 08158228
Jul. 7, 2008 (EP) .................................... 08159790

(51) Int. Cl.
*G01R 27/26* (2006.01)
*G01N 27/22* (2006.01)

(52) U.S. Cl.
CPC .......... *G01N 27/221* (2013.01); *G01R 27/2605* (2013.01)
USPC ............................ 324/663; 324/662; 324/686

(58) Field of Classification Search
CPC ... G01N 27/221; G01N 27/226; G01N 27/22; G01B 7/14; G01B 7/023; G06K 9/0002; G01D 5/24; G01R 27/2605; G01R 27/26
USPC ........................................ 324/663, 662, 686
See application file for complete search history.

(56) References Cited

U.S. PATENT DOCUMENTS 3,936,755 A      2/1976   Sheng
5,247,281 A *   9/1993   Facon et al. ................... 340/562
(Continued)

FOREIGN PATENT DOCUMENTS

EP    0949557 A1    10/1999
GB    2021782 A     12/1979
JP    60029204 A    2/1985

*Primary Examiner* — Amy He

(57) ABSTRACT

A capacitive proximity device for sensing a presence and/or absence of an object in the proximity of an electronic device includes an emission electrode capacitively coupled to a receiver electrode, an oscillator for generating an emission-signal being an alternating electric field between the emission electrode and the receiving electrode, and a sensing circuit connected to the receiving electrode. The sensing circuit receives a measured-signal from the receiver electrode and includes a first synchronous detection circuit together with a low-pass filter for generating an output-signal being proportional to a distance between the object and the electronic device. The sensing circuit further includes a noise-suppresser for reducing noise from the measured-signal before entering the first synchronous detection circuit.

14 Claims, 11 Drawing Sheets

(56) References Cited

U.S. PATENT DOCUMENTS

| | | |
|---|---|---|
| 6,051,981 A | 4/2000 | Gershenfeld et al. |
| 6,418,536 B1 | 7/2002 | Park |
| 6,486,681 B1 | 11/2002 | Weber et al. |
| 6,650,322 B2 | 11/2003 | Dai et al. |
| 6,657,323 B2 | 12/2003 | Muller |
| 2002/0154039 A1 | 10/2002 | Lambert et al. |
| 2003/0051179 A1 | 3/2003 | Tsirkel et al. |
| 2003/0122777 A1 | 7/2003 | Grover |
| 2005/0068289 A1 | 3/2005 | Diefenbaugh et al. |
| 2007/0269012 A1 | 11/2007 | Somers |

\* cited by examiner

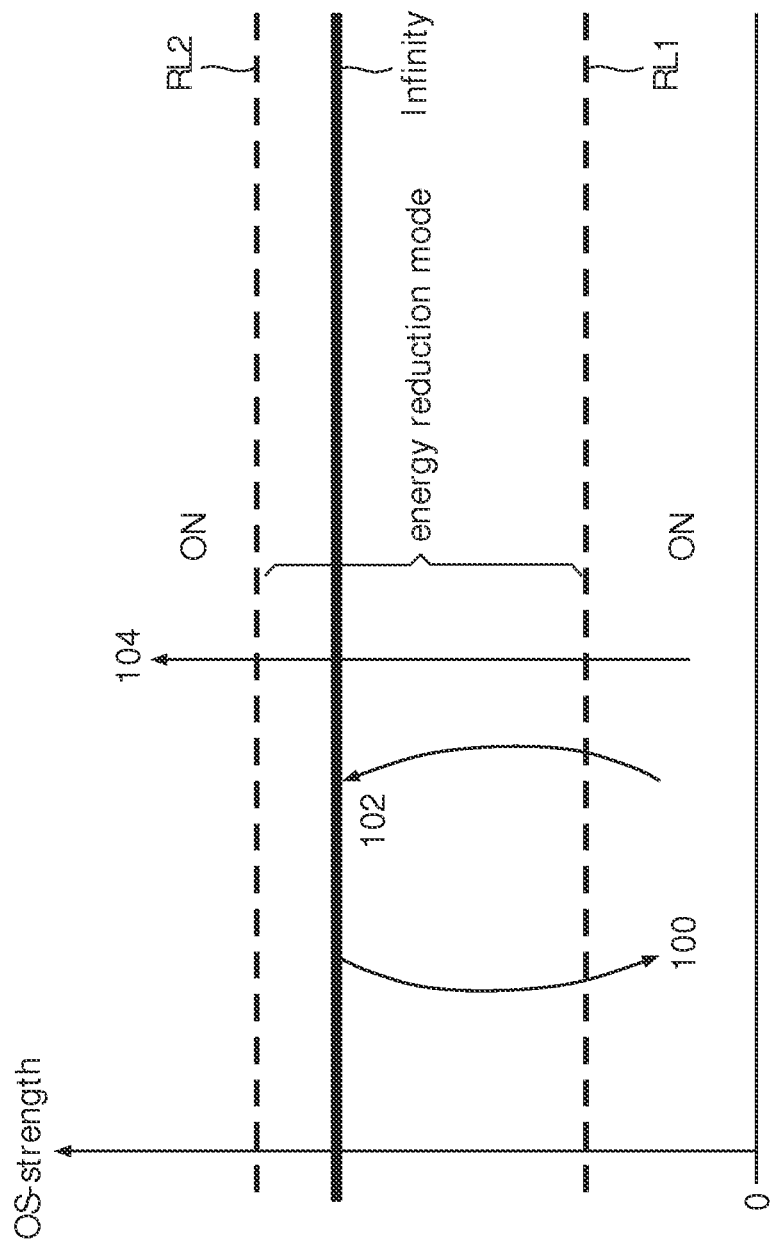

CAPACITIVE PROXIMITY DEVICE AND ELECTRONIC DEVICE COMPRISING THE CAPACITIVE PROXIMITY DEVICE

FIELD OF THE INVENTION

The invention relates to a capacitive proximity device of an electronic device. The invention further relates to an electronic device comprising the capacitive proximity device, and to a sensing circuit for the capacitive proximity device.

BACKGROUND OF THE INVENTION:

Reduction of energy consumption in display devices when the display device is not used, is known, for example, in monitors for personal computers and/or laptops. In such a system, the activity of a user is measured, for example, by detecting key-strokes of the user or mouse-movements of the user. In case the user has not stroke a key for some predetermined time, or has not moved the mouse of the computer and/or laptop for some predetermined time, the display device enters a so called energy reduction mode which may also be called a "sleep mode" in which the display device switches off, or in which the backlight of the display device switches off. However, often the display device switches to the energy reduction mode while the user is, for example, reading a lengthy text on the display device, not striking a key or moving the mouse.

In more advanced energy consumption schemes, the actual presence of a user in front of the display device is sensed. This has as an advantage that the display device does not enter the energy reduction mode as long as the user is in front of the display device. Furthermore, when the user moves away from the display device, the predetermined time after which the energy reduction mode is activated may be reduced, thus further reducing the (unnecessary) power consumption of the display device. Such systems are, for example, known from the US patent application US 2003/0051179 in which a display having a sensor for detecting the absence of a user is disclosed. Alternatively, EP 0 949 557 discloses a similar system in a portable computer. Both documents disclose infrared or ultrasound sensors to detect the presence or absence of a user in front of the display device. The known sensors used in the display device transmit a signal using a transmitter and sense a reflected signal from the user. Alternatively, the US patent application US 2003/0122777 discloses that the sensor may include a camera, SONAR or RADAR systems to detect a distance of the user in front of the display device.

A disadvantage of active infrared and ultrasound sensors are their dependency with respect to the material of the object. Clothing may absorb the transmitted energy too much thereby reducing the detection range or give false distance readings. Also the field of view is often relatively narrow resulting in a sensitive area only in the direct centre line in front of the display device. This may be solved by using more sensors directing in different directions—however this results in a relatively expensive solution. Passive infrared sensors will not react on stationary (warm) objects, so when a person doesn't move enough in front of the monitor, the energy reduction mode will be activated which again may be an unwanted situation.

An alternative sensor for sensing the presence of a person in front of the display device is via a capacitive sensor. The capacitive sensor is, for example, disclosed in U.S. Pat. No. 6,486,681 in which a measuring circuit for a capacitive sensor is disclosed for distance measurement and/or space monitoring. The measuring circuit comprises a phase-dependent rectifier arrangement connected to an analog-to-digital converter.

A drawback of the known capacitive sensor is that the registration of a person by the known capacitive sensor is not reliable enough.

SUMMARY OF THE INVENTION:

It is an object of the invention to provide a capacitive proximity device having improved reliability.

According to a first aspect of the invention the object is achieved with a capacitive proximity device for sensing a presence and/or absence of an object in the proximity of an electronic device, the capacitive proximity device comprising:

an emission electrode capacitively coupled to a receiver electrode, an oscillator for generating an emission-signal being an alternating electric field between the emission electrode and the receiver electrode, and a sensing circuit connected to the receiver electrode, the sensing circuit receiving a measured-signal from the receiver electrode, and comprising a first detection circuit for generating an output-signal being proportional to a distance between the object and the electronic device, the measured-signal comprising noise, and the sensing circuit further comprising noise-suppression means for reducing noise from the measured-signal before entering the first detection circuit.

The inventors have found that the output-signal of the known capacitive sensor when used in an electronic device, specifically a display device, is relatively noisy. Due to this noisy signal the registration of a person by the known capacitive sensor is not reliable enough. The inventors have found that the noisy signal results from the display device itself and/or from the environment of the display device, for example, other display devices having a capacitive proximity device for detecting the presence and/or absence of an object in the neighborhood of the other display device. The display device itself and/or the other display device interfere with the measured-signal. The capacitive proximity device is typically located in a rim around the display of the display device. Because the rim is becoming relatively small, the emission electrode and the receiver electrode are also located relatively close to the display of the display device. Because the display also generates a varying electric field, the noise resulting from the relatively small distance to the display of the display device causes too much noise for reliably identify an object and/or person. This noise has a relatively broad frequency spectrum. The synchronous detection together with the low-pass filter in the known capacitive sensor is used to filter noise from the measured-signal. However, noise having frequency components close to the generated emission frequency and thereby lying within the transmission band of the band-pass amplifiers, is not adequately filtered by the band-pass amplifiers. Due to the large amplitude of the in-band noise, the amplifiers and synchronous detector may clip, resulting in in-adequate filtering and mis-functioning of the circuitry, giving erroneous object presence detection.

The inventors have found that additional noise-suppression techniques are required when applying the known capacitive sensors in a display device. To improve the reliability of the capacitive proximity device according to the invention, the capacitive proximity device comprises noise-suppression means for reducing noise from the measured-signal before entering the synchronous detection circuit. By applying the noise-suppression means before the first synchronous detection circuit, the noise present in the measured-signal is reduced before it is amplified. As such, the adding of the noise-suppression means prevents the amplifier stages in the sensing circuit to clip, causing the detection of the person or object to be more reliable.

The sensing circuit in the capacitive proximity sensor according to the invention performs method steps comprising:
  receiving a measured-signal from the receiver electrode,
  generating the output-signal via a synchronous detection method and by low-pass filtering the output of the synchronous detection method, and
  applying a noise-suppression method for reducing noise from the measured-signal before applying the synchronous detection method.

These method steps may be performed by a computer program product comprising instructions for causing a processor to perform the above listed method steps.

The synchronous detection may, for example, be done using synchronous rectification using a switching rectifier which is driven using a reference-signal which is substantially in phase with the emission-signal. Typically, the first synchronous rectifier switches substantially at the zero-crossing of the reference-signal or emission-signal. Subsequently a first low-pass filter and an amplifier are used to extract and amplify the signal being indicative of the presence of absence of a person or object. This signal may be stationary or slow-varying, in which the slow-varying signal may be an indication that the object is moving.

The generated output-signal may be compared with a first proximity reference level using, for example, a comparator. The output-signal increases when a distance between the object and the electronic device increases. So, when the output signal increases to above the first proximity reference level, the electronic device considers the user to be absent and switches to the energy reduction mode.

In an embodiment of the capacitive proximity device, the noise-suppression means comprises a first differential amplifier for generating a noise-signal comprising at least a part of the noise from the measured-signal by subtracting a correction-signal from the measured-signal, the correction-signal having substantially the same frequency and phase as the emission-signal and having an amplitude proportional to the sensed-emission-signal. Such a noise-signal may, for example, be used in the capacitive proximity device to generate active noise suppression. The amplitude of the correction-signal is proportional to the sensed-emission-signal, and preferably comprises the same amplitude as the sensed-emission-signal. To suppress the in-band noise which may be present in the measured-signal, the noise-suppression means reconstructs the noise-component in the measured-signal by subtracting the correction-signal from the measured-signal. As the correction-signal has the same frequency as the emission-signal and has an amplitude proportional to the sensed-emission-signal, the differential amplifier removes at least a part of the sensed-emission-signal from the measured-signal, generating the noise-signal indicative of the noise in the measured-signal. This noise-signal may subsequently be used to generate a substantially noise-less copy of the sensed-emission-signal.

The sensing circuit in the capacitive proximity sensor according to the invention may perform method steps comprising:
  receiving a correction-signal having substantially the same frequency as the emission-signal and having an amplitude proportional to the sensed-emission-signal, and
  subtracting the correction-signal from the measured-signal for generating the noise-signal.

These method steps may be performed by a computer program product comprising instructions for causing a processor to perform the above listed method steps.

In an embodiment of the capacitive proximity device, the capacitive proximity device comprises a further receiver electrode shielded from the emission-signal for sensing a noise-signal comprising at least a part of the noise resulting from the display device. The inventors have found that a major part of the noise results from the display of the display device. By arranging the further receiver electrode shielded from the emission-signal and such that this further receiver electrode typically only senses the noise coming from the display of the display device, this noise-signal from the further receiver electrode may be used to actively reduce the noise from the measured-signal, for example, by subtracting the noise-signal from the measured-signal using a second differential amplifier.

The shielding of the further receiver electrode may be done by using substantially narrow noise receiving electrode in close proximity of the active display unit. The emission signal receiving electrode preferably positioned on top of the noise-receiving electrode and as such substantially shielding the noise-receiving electrode from the emission signal.

In an embodiment of the capacitive proximity device, the noise-suppression means further comprises a variable gain amplifier, a second synchronous detection circuit together with a second low-pass filter, and an integrator circuit, the second synchronous detection circuit together with the second low-pass filter receiving the noise-signal for generating an effective amplitude of the sensed-emission-signal, the integrator circuit receiving the effective amplitude and comparing the effective amplitude with a reference level for generating a gain-signal being provided to the variable gain amplifier and defining a gain of the variable gain amplifier, the variable gain amplifier receiving the emission-signal and the gain-signal and adapting the amplitude of the emission-signal in accordance with the gain-signal to generate the correction-signal. The noise-signal comprises all the noise from the measured-signal, while the sensed-emission-signal is suppressed, preferably completely suppressed. The correction-signal is associated with the sensed-emission-signal in that the correction-signal is a substantially noise-free copy of the sensed-emission-signal. The correction-signal is generated using the noise-signal and applying further synchronous detection using the second synchronous detection circuit together with the second low-pass filtering to the noise-signal, removing a major part of the noise and only providing the effective amplitude of the sensed-emission-signal being stationary or slow-varying amplitude of the sensed-emission-signal. The low-frequency remaining signal is compared, for example, against ground level to generate the gain signal being indicative for the low-frequency part of the sensed-emission-signal. This gain-signal is subsequently used to modulate the emission-signal. The emission-signal may be considered to be a substantially noise-free signal and the gain-signal may be considered to mainly comprise the low-frequency sense-information required to indicate whether a person or object is in the vicinity of the capacitive proximity device. Modulating the substantially noise-free emission-signal using the gain-signal generates a substantially noise-free copy of the sensed-emission-signal which includes the sensed vicinity information. This noise-free copy may further be used to reliably generate the output-signal being a reliable indication of the presence and/or absence of a person or object in the neighborhood of the capacitive proximity device according to the invention.

The sensing circuit in the capacitive proximity sensor according to the invention may perform method steps comprising:
generating an effective amplitude via a further synchronous detection method and by low-pass filtering the output of the further synchronous detection method,
comparing the effective amplitude to a reference level for generating a gain-signal, and
adapting the amplitude of the emission-signal in accordance with the gain-signal to generate the correction-signal.

These method steps may be performed by a computer program product comprising instructions for causing a processor to perform the above listed method steps.

In an embodiment of the capacitive proximity device, the noise-suppression means comprises a second differential amplifier for generating a noise-reduced measured-signal subsequently provided to the first detection circuit for generating the output-signal, the second differential amplifier generating the noise-reduced measured-signal by subtracting the noise-signal from the measured-signal. Between the second differential amplifier and the first synchronous detection circuit, a band-pass amplification step may be present to amplify the noise-reduced measured-signal before it enters the first synchronous detection circuit. The noise-signal is produced by subtracting the correction-signal (being the substantially noise-free copy of the sensed-emission-signal) from the measured-signal. As such, the noise-signal comprises the substantially isolated noise which was previously in the measured-signal. This isolated noise may be subtracted from the measured-signal to at least partially remove the noise before the signal enters the first synchronous detection circuit. By actively removing the noise from the measured-signal using the noise-signal, the reliability of the output-signal is improved.

The sensing circuit in the capacitive proximity sensor according to the invention may perform method steps comprising:
generating a noise-reduced measured-signal by subtracting the noise-signal from the measured-signal, and
generating the output-signal by applying the detection method to the noise-reduced measured-signal.

These method steps may be performed by a computer program product comprising instructions for causing a processor to perform the above listed method steps.

In an embodiment of the capacitive proximity device, the correction-signal is provided to the first detection circuit for generating the output-signal. Again, the correction-signal may be amplified using a band-pass amplification step before the amplified correction-signal enters the first synchronous detection circuit. The inventors have found that, because the correction-signal is a substantially noise-free copy of the sensed-emission-signal, the correction-signal may beneficially be used to generate the output-signal rather than using the measured-signal. In this alternative embodiment of active noise suppression, the correction-signal is supplied directly to the first synchronous detection circuit (possibly after having been amplified via the band-pass amplification step), instead of generating the noise-reduced measured-signal by subtracting the noise-signal from the measured-signal as indicated before. This alternative embodiment of active noise suppression requires fewer components as it typically requires one less differential amplifier (the second differential amplifier). Generally, before the noise-reduced measured-signal is provided to the first synchronous detection circuit, the noise-reduced measured-signal passes a band-pass filter and an amplifier. The band-pass filter is used to further suppress noise. Amplification is preferably done using the alternating signal as this generally has a cost benefit in that relatively inexpensive components may be use for the amplification. When using the correction-signal rather than the noise-reduced measured-signal, the additional band-pass filter before the amplifier may be omitted, further reducing the cost of the active noise-reduction circuit according to the invention.

The sensing circuit in the capacitive proximity sensor according to the invention may perform the additional method step, in that the method comprises:
generating the output-signal by applying the detection method to the correction-signal.

These method steps may be performed by a computer program product comprising instructions for causing a processor to perform the above listed method steps.

The active noise-reduction circuit as shown and explained may be performed in any system requiring general signal processing by receiving an alternating measured-signal comprising information in a narrow-frequency part of the signal and comprising a relatively broad frequency range of noise, Also , the active noise-reduction may be performed at a different position in the sensing circuit or at multiple positions in a sensing circuit compared to what is shown and explained above. Filially, the active noise- reduction circuit may be used in other devices requiring noise-reduction of a measured-signal, for example, other devices using synchronous detection methods, and not only in a capacitive proximity device for a electronic device.

In an embodiment of the capacitive proximity device, the noise-suppression means comprises a beat-detector for analyzing the measured-signal and/or the output-signal to identify a regular and/or periodic signal component other than the frequency of the emission-signal in the measured-signal. This regular and/or periodic signal component may result from the generation of the current picture shown on the display device which may comprise a relatively regular and/or periodic signal. The generation of the current picture may comprise a regular frequency which interferes with the frequency of the emission-signal and thus may not be filtered via the known synchronous detection. Such an interfering signal may relatively easily be detected using several known hardware and/or software arrangement.

The beat-detector as disclosed here may be added to the active noise-suppression methods as already disclosed. However, the adding of such beat-detector may also be in other systems requiring general signal processing in which a signal having a predetermined frequency is emitted and an associated signal is subsequently measured. In any of these systems the beat-detector as disclosed in here and in the remainder of the text may be beneficially applied to detect regular and/or periodic signal components an' the frequency of the emission signal to avoid these regular and/or periodic signal components or to select a frequency of the emission signal in which the interference of the identified regular and/or periodic signal components is minimal.

The beat-detector as disclosed above adapts the frequency of the emission-signal to reduce an interfering signal having a regular and/or periodic signal component in the measured-signal. Although the analysis of the frequency of the interfering signal component may be done behind the first synchronous detector, the adaptation for reducing the noise from the measured signal is done by altering the frequency of the emission signal at the oscillator, and thus is done before the measured-signal enters the first synchronous detection circuit.

Finally, the beat-detector may be used in other devices and not only in a capacitive proximity device for an electronic device.

The noise-suppressing means in the capacitive proximity sensor according to the invention may comprise method steps, which comprise:
  receiving the measured-signal and/or the output-signal, and
  analyzing the measured-signal and/or output-signal to identify a regular and/or periodic signal component other than the frequency of the emission-signal in the measured-signal.

These method steps may be performed by a computer program product comprising instructions for causing a processor to perform the above listed method steps.

The beat detection may relatively easily be performed in a programmable controller, for example, a microcontroller. The output-signal of the capacitive proximity device is indicative for the distance between the object and the capacitive proximity device. Generally an object typically does not move in a substantially regular movement in front of the capacitive proximity device. When such a substantially regular movement is detected over, for example, a predetermined time interval, the regular movement may be noise resulting from the display device or may be noise resulting from a further display device, for example, also comprising a further capacitive proximity device. Such a regular and/or periodic signal may not fully be removed via the synchronous detection to generate the output-signal and may manifest itself as a signal indicating a varying distance between the object and the capacitive proximity device. This further capacitive proximity device may influence the measured-signal of the capacitive proximity device and as such provide an erroneous variation in the distance between the object and the capacitive proximity device. Altering the frequency of the emission-signal may reduce the regular and/or periodic component in the measured-signal, reducing the regular noise in the measured-signal which cannot be removed sufficiently using the synchronous detection.

In an embodiment of the capacitive proximity device, the beat-detector comprises:
  means for receiving the measured-signal and/or output-signal being indicative of a distance between the object and the capacitive proximity device,
  means for analyzing the measured-signal and/or output-signal for detecting a regular and/or periodic distance variation of the object with respect to the capacitive proximity device, the regular and/or periodic distance variation being indicative for the regular and/or periodic signal component in the sensed-emission-signal,
  if such regular and/or periodic distance variation is identified: the capacitive proximity device comprises means for sending a frequency-signal to the oscillator for altering the frequency of the emission-signal.

The means for analyzing the measurement-signal and/or output-signal may, for example, comprise a Fourier-transform algorithm of which different algorithms are known in the art. Such a Fourier-transform algorithm may very suitably be done in software, especially when using the output-signal for the analysis, because the output signal is a stationary signal or a slow-moving signal which would not require a fast analog-to-digital converter. Alternatively different means for analyzing the measurement-signal and/or output signal for finding a regular and/or periodic component in the measured signal may be used.

The beat-frequency which is interfering with the sensed-emission-signal typically has a frequency which is relatively low, for example, 10 Hertz and below.

Interference which has a higher frequency than 10 Hertz is filtered by the first low-pass filter behind the first synchronous detection circuit and only marginally influences the output-signal.

The noise-suppressing means in the capacitive proximity sensor according to the invention may comprise method steps, which comprise:
  receiving the measured-signal and/or output-signal being indicative of a distance between an object and the capacitive proximity device,
  analyzing the measured-signal and/or output-signal for detecting a regular and/or periodic distance variation of an object with respect to the capacitive proximity device, the regular and/or periodic distance variation being indicative for a regular and/or periodic signal component in the measured-signal,
  if such regular and/or periodic distance variation is identified: send a frequency-signal to the oscillator for altering the frequency of the emission-signal.

These method steps may be performed by a computer program product comprising instructions for causing a processor to perform the above listed method steps.

In an embodiment of the capacitive proximity device, the oscillator is arranged to switch to further frequency in a predefined range of frequencies around a center frequency. The center frequency, for example, is 75 kHz and the band-pass amplifiers are chosen to have the center of the band-pass filter substantially corresponding to the center frequency of the oscillator. The frequency-signal may comprise, for example, a three-bit signal allowing 8 different frequencies, for example, each separated by 800 Hz to select from to reduce the regular and/or periodic signal component from the measured-signal. Using a three-bit signal reduces the complexity of the noise-suppression means while allowing a shift in the oscillator frequency to reduce the regular and/or periodic signal component from the measured-signal.

Furthermore, the change of the frequency of the oscillator should be limited due to the use of band-pass filters. Due to the band-pass filters being present, the phase at which the synchronous detection is performed may not fully correspond to the phase of the emission-signal generated by the oscillator, especially when the frequency of the emission-signal is shifted from the center frequency. This (relatively small) shift in the phase between the emission-signal and the detection phase of the synchronous detector results from the band-pass filter not being fully centered around the frequency of the emission-signal. As a result, the amplitude of the output-signal typically is reduced, thus reducing the sensitivity of the capacitive proximity device. By switching to different frequencies within a predefined range of frequencies, this range of frequencies may be chosen such that the reduction of the output-signal remains limited.

In an embodiment of the capacitive proximity device, the beat-detector is arranged for detecting a regular and/or periodic signal component having a frequency below 20 Hertz. The beat-frequency which is interfering with the sensed-emission-signal typically has a frequency which is relatively low, for example, 20 Hertz and below. Interference which has a higher frequency than 20 Hertz is filtered by the low-pass filter behind the synchronous detection circuit and only marginally influences the output-signal.

In an embodiment of the capacitive proximity device, the capacitive proximity device further comprises a phase-control circuit for minimizing a phase difference between a reference-signal and the sensed-emission-signal, the reference-signal being used for triggering the first detection circuit being a first synchronous detection circuit and/or the second synchronous detection circuit. In an embodiment of the capacitive proximity device, the reference-signal is substantially the same as the emission-signal generated by the oscillator, or the reference-signal is a signal directly derived from the emission-signal. As indicated before, there may be a phase-difference between the reference-signal and the measured-signal, for example, due to a shift of the frequency of the emission-signal relative to the center frequency of the band-pass filter by tuning the oscillator to avoid a regular and/or periodic signal component in the measured-signal by the beat-detector. When such a phase-difference is present, the sensitivity of the capacitive proximity device is not optimal. By applying a phase-control circuit for shifting the phase of the reference-signal to substantially coincide with the phase of the measured-signal, the signal-strength of the measured signal is maximized and thus the sensitivity of the capacitive proximity device is maximized.

The noise-suppressing means in the capacitive proximity sensor according to the invention may comprise a method step, which comprises:
  minimizing a phase difference between a reference-signal and the measured-signal, the reference-signal being used for triggering the first detection circuit being a first synchronous detection circuit and/or the second synchronous detection circuit.

These method steps may be performed by a computer program product comprising instructions for causing a processor to perform the above listed method steps.

In an embodiment of the capacitive proximity device, the phase-control circuit comprises a variable phase-controller, a third synchronous detection circuit together with a third low-pass filter, and a second integrator circuit, the third synchronous detection circuit together with the third low-pass filter receiving the measured-signal and detecting the measured-signal using a phase-shifted reference-signal being 90 degrees shifted in phase with respect to the reference-signal, the second integrator circuit comparing the output of the third low-pass filter with a reference level (for example, ground) for generating a phase-control-signal being provided to the variable phase-controller and defining a phase of the reference-signal. The adjustment of the reference signal is often done manually, for example, using phase-adjustment in lock-in amplifiers. Alternatively, an automated phase-adjustment may be used, for example, using multiplication with quadrature reference signals, and using the square root of the sum of the two squared outputs. However, such automated phase-adjustment requires powerful processing and thus is relatively expensive. The automatic phase-control circuit as currently disclosed prevents manual or factory adjustment of the capacitive proximity device and reduces cost.

Due to the use of the third synchronous detection circuit which switches at a frequency which is 90 degrees shifted with respect to the reference-signal, the output of the third synchronous detection circuit is substantially zero when the phase of the reference-signal corresponds to the phase of the measured-signal. However, when there is a shift in the phase between the two signals, the second integrator circuit generates a phase-control-signal being proportional to the sensed phase-shift. This phase-control-signal may directly be used for controlling the variable phase-controller to adapt the phase of the reference-signal such that the phase difference between the reference-signal and the measured-signal is substantially zero.

A further benefit of this embodiment is that it automatically corrects for discrepancies in the phase between the reference-signal and the measured-signal which may be caused due to the shifting of the emission-frequency with respect to the center frequency of the band-pass filter by the oscillator initialized by the beat-detector. Combining the phase-control circuit with the beat-detector, the range over which the frequency may be altered to prevent regular and/or periodic signal components may be expanded and the sensitivity of the capacitive proximity device may remain relatively high.

The phase-control circuit as disclosed here may be added to the active noise suppression methods. However, the adding of such phase-control circuit may also be in other systems requiring general signal processing in which a signal having a predetermined frequency is emitted and an associated signal is subsequently measured. In any of these systems the phase-control circuit as disclosed' in here and in the remainder of the text may be beneficially applied to synchronize the frequency at which the synchronous detector is driven with respect to the frequency of the treasured-signal, As a result, a relatively inexpensive and accurate phase- control circuit is obtained.

The phase-control circuit as disclosed above adapts the phase of the reference-signal to maximize the output of the synchronous detection circuit. As such the adaptation to maximize the output of the synchronous detection circuit and thus for reducing the noise from the measure- signal is done by altering the phase of the reference-signal before the measured-signal enters the first synchronous detection circuit.

Finally, the phase-control circuit may be used in other devices and not only in a capacitive proximity device for an electronic device.

The noise-suppressing means in the capacitive proximity sensor according to the invention may comprise method steps, which comprise:
  generating a phase-control signal by detecting the measured-signal using a third synchronous detector detecting at a detection frequency being 90 degrees shifted in phase with respect to the reference-signal, and by comparing the output of the third synchronous detector to a reference level, and
  adapting the phase of the reference-signal in accordance with the phase-control signal to be in phase with the measured-signal.

These method steps may be performed by a computer program product comprising instructions for causing a processor to perform the above listed method steps.

In an embodiment of the capacitive proximity device, the emission-signal is the reference signal.

In an embodiment of the capacitive proximity device, the capacitive proximity device comprises a first comparator for comparing the output-signal to a first proximity reference-level for determining the presence and/or absence of the object, and wherein the capacitive proximity device comprises a second comparator for comparing the output-signal to a second proximity reference-level for determining the presence and/or absence of the object at close range.

The comparator may be a separate comparator, or may be included in a microcontroller or in programmed processing steps of a microcontroller. In the remainder of the text, the text "close range" indicates a distance close to the capacitive proximity device, for example, a distance of 20 millimeter or less.

The generated output-signal may be compared with the first proximity reference level using, for example, the comparator. The output-signal increases when a distance between the object and the electronic device increases. So, when the output signal increases to above the first proximity reference level, the display device considers the user to be absent and switches to the energy reduction mode.

Alternatively, because the output-signal is proportional to the distance between the object and the display device, the output signal may be used to control other parameters of the display device, such as the intensity of the light emitted from the display device, for example, the intensity of the backlight of the display device (in case of a liquid crystal display device). The output-signal may be used also for other parameters, for example, altering the color of the display device, or adapting the volume of the speakers of the display device in relation to the distance of the object or person to the display device, and, for example, adapting the magnification of the display device, or, for example, increasing the font when a user is located further away from the display device.

The capacitive proximity device, for example, generates a specific output-signal level referring to a situation in which no person is in the neighborhood of the display device. This signal level may be indicated as "infinity-signal level" indicating that this is the maximum signal level when nobody is in the neighborhood of the display device. When the output-signal level decreases the object or person approaches the display device. The capacitive proximity device according to the invention may, for example, be configured to switch off the energy reduction mode when the output-signal level is below the first proximity reference level. The display device, for example, switches on and displays the current information to the user. The capacitive proximity device according to the invention may also have a second proximity reference level which is substantially above the "infinity-signal level". This second proximity reference level is used to indicate a situation in which the object or person is very close to the capacitive proximity device, for example, 20 millimeter or less. When the person or object is very close to the capacitive proximity device, the person or object starts to be part of the capacitive proximity device and increases the capacitive coupling between the emission electrode and the receiver electrode considerably. In such a situation, the output-signal typically substantially exceeds the "infinity-signal level". This may, for example, occur when a person wants to adapt settings of a display device and has to operate switches at the outer surface of the display device. When such high signal is detected, the display device must remain switched on and should not start an energy reduction mode to ensure that the user may, for example, see the adaptations he is performing. To avoid the display device to switch to the energy reduction mode during the relatively quick change from the output-signal level below the first proximity reference level to the output-signal level above the second proximity reference level, a short delay time may be incorporated before the display device switches to the energy reduction mode.

The noise-suppressing means in the capacitive proximity sensor according to the invention may comprise method steps, which comprise:
  comparing the output-signal to a first proximity reference-level for determining the presence and/or absence of the object, and
  comparing the output-signal to a second proximity reference-level for determining the presence and/or absence of the object at close range.

These method steps may be performed by a computer program product comprising instructions for causing a processor to perform the above listed method steps.

In an embodiment of the capacitive proximity device, the capacitive proximity device comprises means for performing periodic calibration of the capacitive proximity device during an absence of the object for correcting for changes in the surroundings of the capacitive proximity device. The calibration may, for example, include defining the first and second proximity reference levels.

The means for performing periodic calibration may be a controller having a timer or other input means such as, for example, a temperature and/or humidity sensor which may be used to decide whether a next calibration of the system may be required. This controller may be part of an on-board microcontroller or a different controller. Changes in the surroundings may include changes in the static objects which are in the surroundings and which influence, for example, the "infinity-signal level". Alternatively, changes to the surroundings may also include changes in the environment around the capacitive proximity device, such as changes in the temperature, humidity etc which have an influence to the signal strength of the capacitive proximity device.

The noise-suppressing means in the capacitive proximity sensor according to the invention may comprise a method step, which comprises:
  performing periodic calibration of the capacitive proximity device during an absence of the object for correcting for changes in the surroundings of the capacitive proximity device.

This method step may be performed by a computer program product comprising instructions for causing a processor to perform the above listed method steps.

BRIEF DESCRIPTION OF THE DRAWINGS

These and other aspects of the invention are apparent from and will be elucidated with reference to the embodiments described hereinafter. In the drawings:

FIG. 7 shows the first proximity reference level and the second proximity reference level.

The Figures are purely diagrammatic and not drawn to scale. Particularly for clarity, some dimensions are exaggerated strongly. Similar components in the Figures are denoted by the same reference numerals as much as possible.

DETAILED DESCRIPTION OF THE PREFERRED EMBODIMENTS

Figure 1:
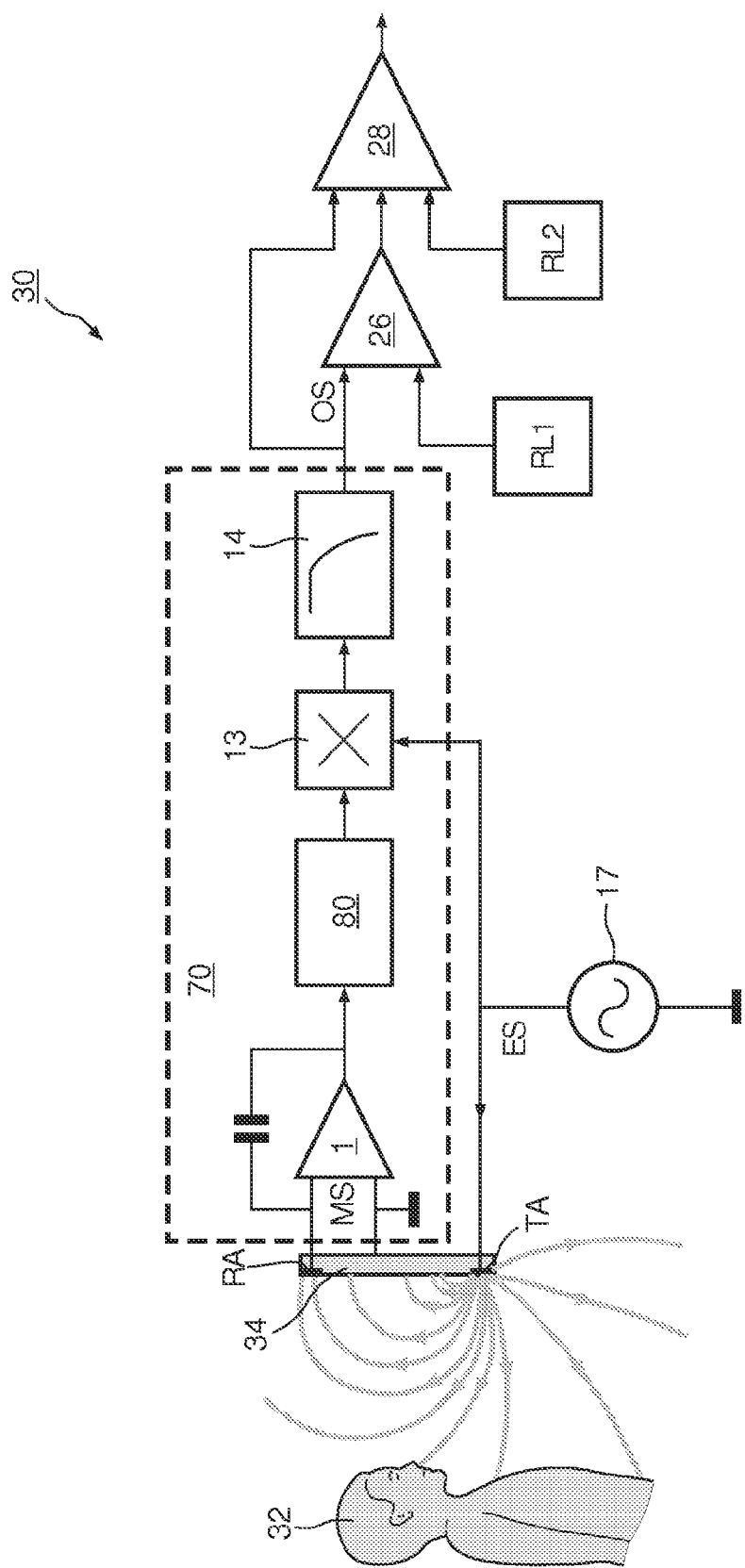
FIG. 1 shows a schematic representation of a capacitive proximity device according to the invention.

FIG. 1 shows a schematic representation of a capacitive proximity device 30 according to the invention. The capacitive device 30 is arranged at an electronic device, for example, a display device 34 and typically at the rim of the display device 34. The capacitive proximity device 30 comprises an emission electrode TA, in the example shown in FIG. 1 arranged at the bottom-rim of the display device 34, and a receiver electrode RA, in the example shown in FIG. 1 the receiver electrode RA is arranged at the top-rim of the display device 34. An oscillator 17 is connected to the emission electrode TA and generates an emission signal ES which is emitted via the emission electrode TA to generate an alternating electric field (indicated in FIG. 1 with the curved lines comprising an arrow which originate from the emission electrode TA. The capacitive proximity device 30 further comprises a sensing circuit 70 connected to the receiver electrode RA and arranged for detecting and amplifying the remainder of the emission signal ES, received via the receiver electrode RA. The sensing circuit 70 comprises a first synchronous detection circuit 13 for synchronous detecting the information from the measured-signal MS. The first synchronous detection circuit 13 also receives the emission-signal ES or a signal having a similar frequency as the emission-signal ES for enabling the first synchronous detector 13 to detect the measured-signal MS at substantially the same frequency as the emission-signal ES. After the synchronous detection circuit 13, the signal is filtered using a first low-pass filter 14 to isolate only the low-frequency content of the measured-signal MS which constitutes the output-signal OS comprising the information from the capacitive proximity device 30.

The capacitive proximity device 30 further comprises a first comparator 26 for comparing the output-signal OS level with a first proximity reference-level RL1. In a preferred embodiment, the capacitive proximity device 30 further comprises a second comparator 28 for comparing the output-signal OS level with a second proximity reference-level RL2.

The generated output-signal OS is proportional to a distance between an object 32 or person 32 and the capacitive proximity device 30. As the object 32 or person 32 typically is grounded, they attract field-lines from the electric field emitted by the emission electrode TA, As a result, when the distance between the object 32 and/or person 32 and the capacitive proximity device 30 decreases, the signal strength of the output-signal OS is reduced. As a consequence, when the signal strength of the output-signal OS is below the first proximity reference-level RL1 (see also FIG.) the capacitive proximity device 30 considers that the person 32 is close to the display device 34 and thus switches on the display device 34, When the person moves away from the capacitive proximity device 30, the signal strength of the output-signal OS increases again, When the signal strength of the output-signal OS is above the first proximity reference level, the capacitive proximity device 30 considers that the person has left the display device 34 and thus the capacitive proximity device 30 signals the display device 34 to go into a power-save mode also indicated in this document as energy reduction mode. In this energy-saving mode, the backlight (not shown) of the display device 34 may be switched off or reduced to a lower intensity and/or the refresh-rate of the displaying of the image on the display device 34 may be reduced.

Alternatively, because the output-signal OS is proportional to the distance between the object 32 and the display device 34, the output signal may be used to control other parameters of the display device, such as the intensity of the light emitted from the display device 34, altering the color of the display device 34, or adapting the volume of the speakers (not shown) of the display device 34 in relation to the distance of the object or person to the display device 34, and, for example, adapting the magnification of the image displayed on the display device 34, or, for example, increasing the font when the person 32 is located further away from the display device 34.

The capacitive proximity device 30, for example, generates a specific output-signal OS level referring to a situation in which no person is in the neighborhood of the display device 34. This signal level may be indicated as "infinity-signal level" (see FIG. 7) indicating that this is the maximum output-signal OS level when nobody is in the neighborhood of the display device 34.

The capacitive proximity device 30 according to the invention may also have the second proximity reference level RL2 (see also FIG. 7) which is substantially above the "infinity-signal level". This second proximity reference level RL2 is used to indicate a situation in which the object or person 32 is very close to the capacitive proximity device 30, for example, 20 millimeter or less. When the person 32 is very close to the capacitive proximity device 30, the person 32 starts to be part of the capacitive proximity device 30 and increases the capacitive coupling between the emission electrode TA and the receiver electrode RA considerably. In such a situation, the output-signal OS typically substantially exceeds the "infinity-signal level". This may, for example, occur when the person 32 wants to adapt settings of a display device 30 and has to operate switches at the outer surface of the display device 34, for example at the rim of the display device 34. When such high output-signal OS is detected, the display device 34 must remain switched on and should not start an energy reduction mode to ensure that the person 32 may, for example, see the adaptations he is performing. To avoid the display device 34 to switch to the energy reduction mode during the relatively quick change from the output-signal OS level below the first proximity reference level RL1 to the output-signal OS level above the second proximity reference level RL2, a short delay time (not shown) may be incorporated before the display device 34 switches to the energy reduction mode.

Figure 2:
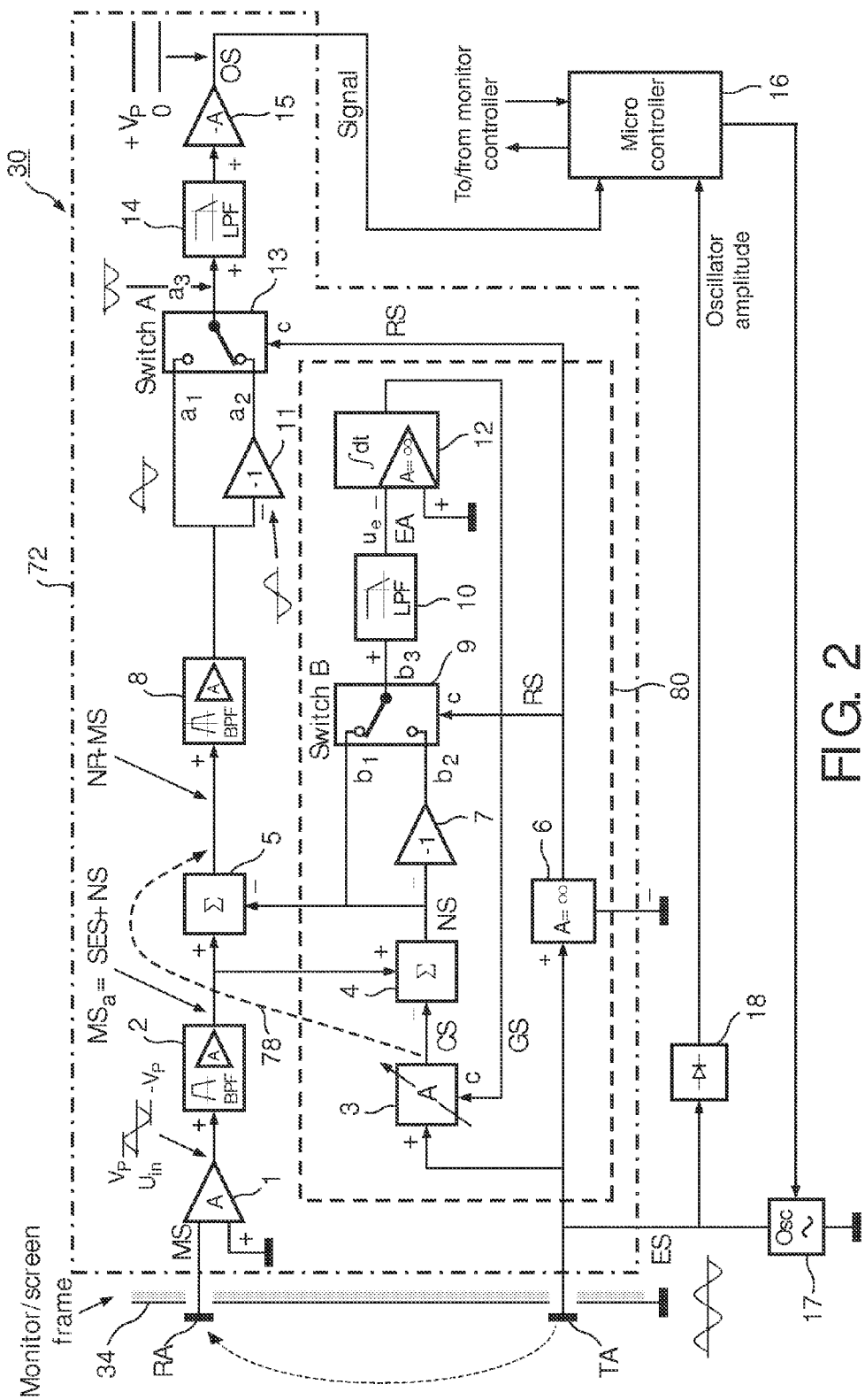
FIG. 2 shows functional block-diagram of the capacitive proximity device comprising an active noise suppression circuit according to the invention.
Figure 3A:
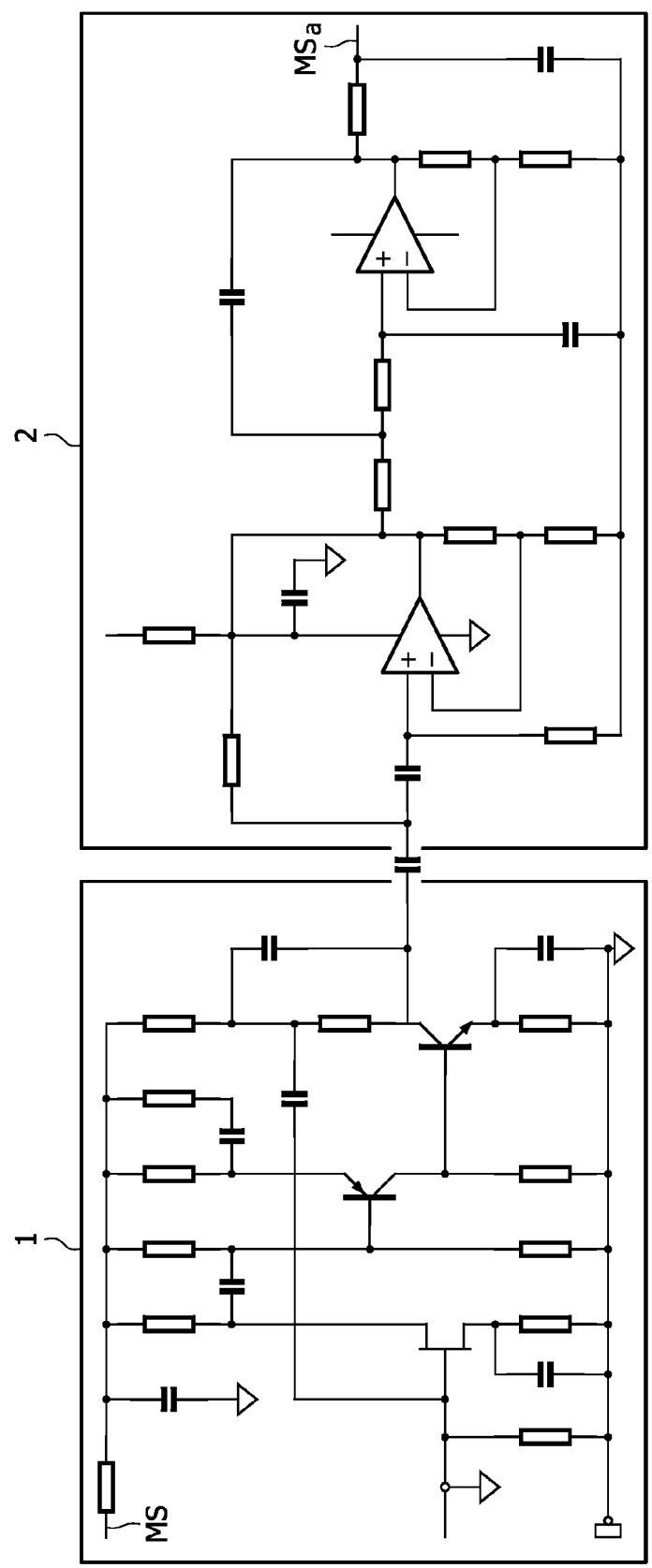
FIG. 3 shows an actual electronic schematic for the capacitive proximity device comprising active noise suppression circuit.
Figure 3B:
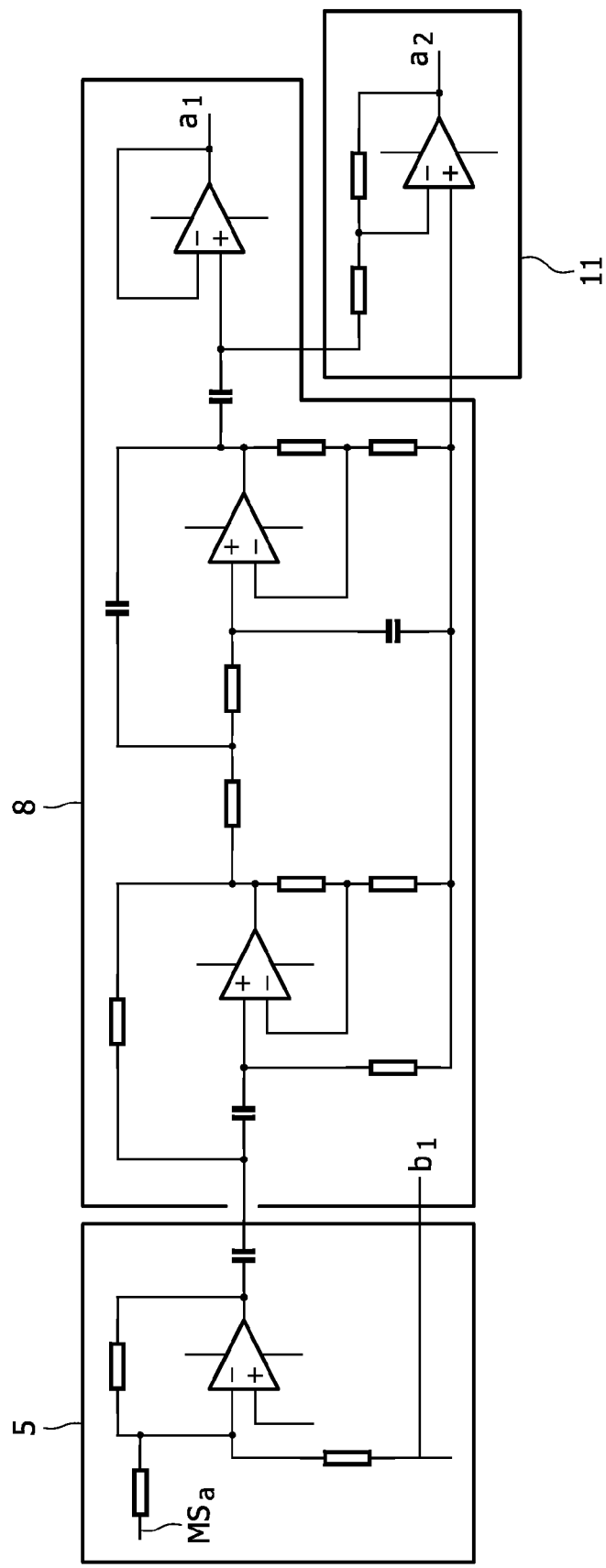
Figure 3C:
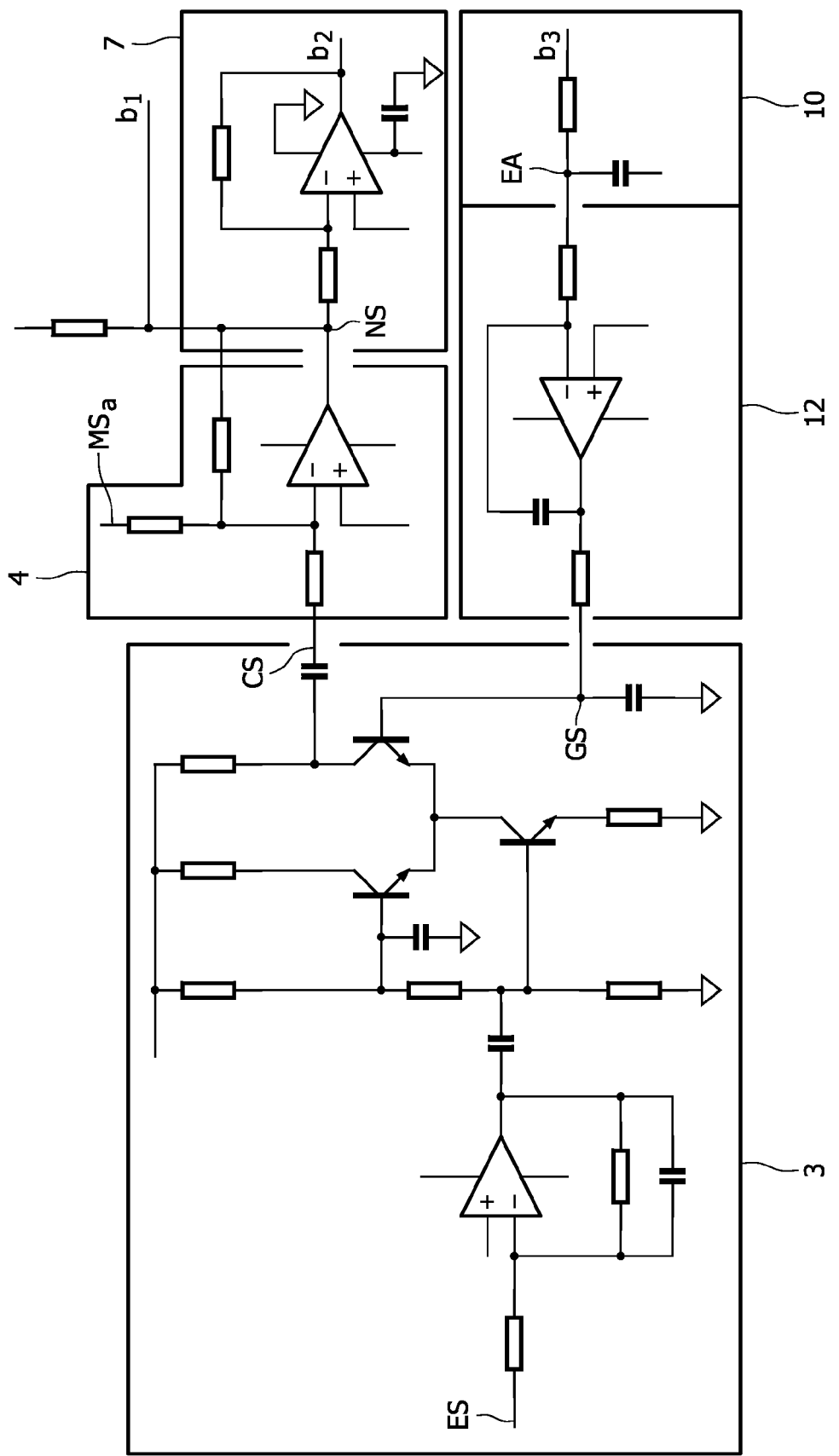
Figure 3D:
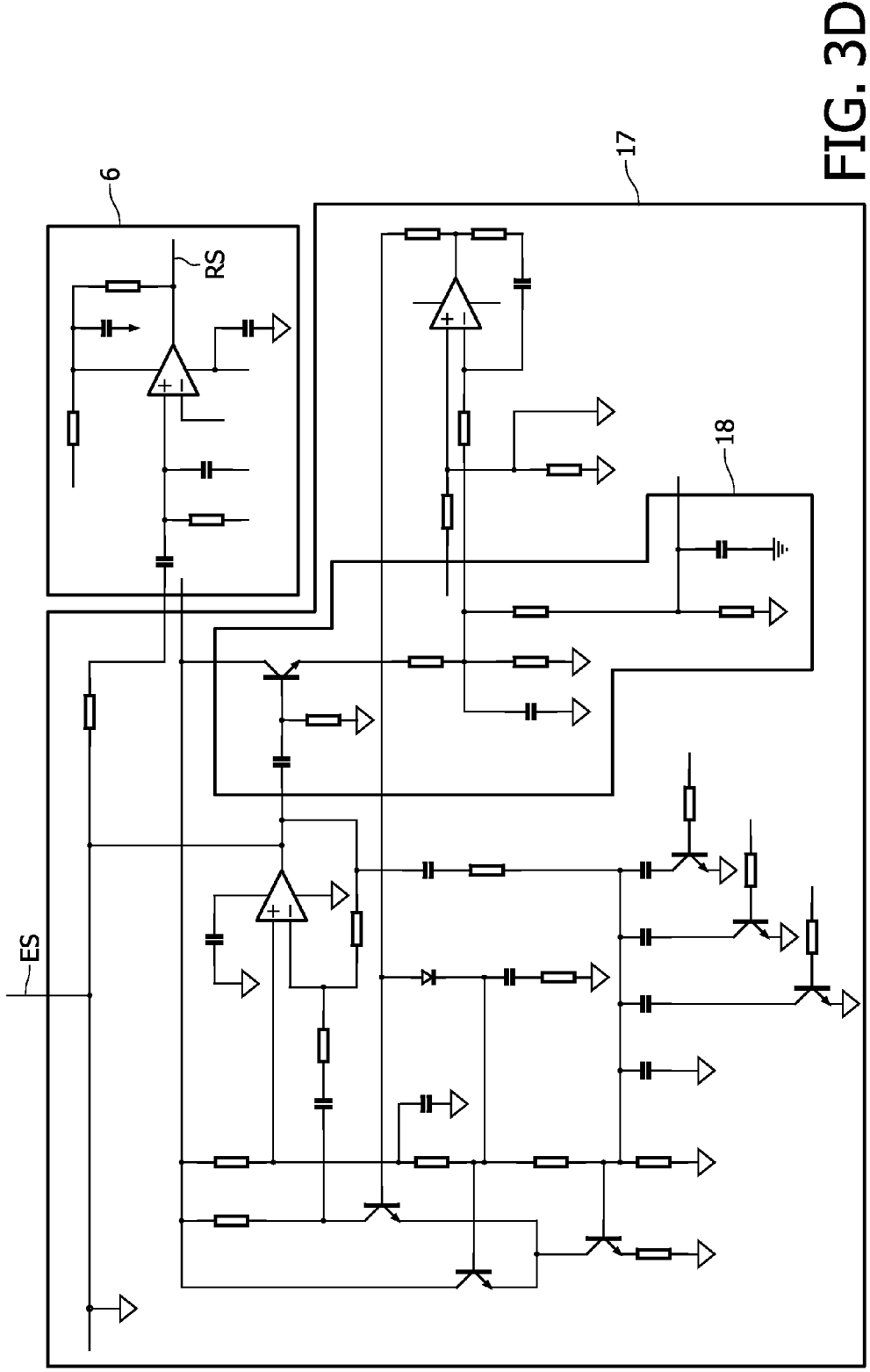
Figure 3E:
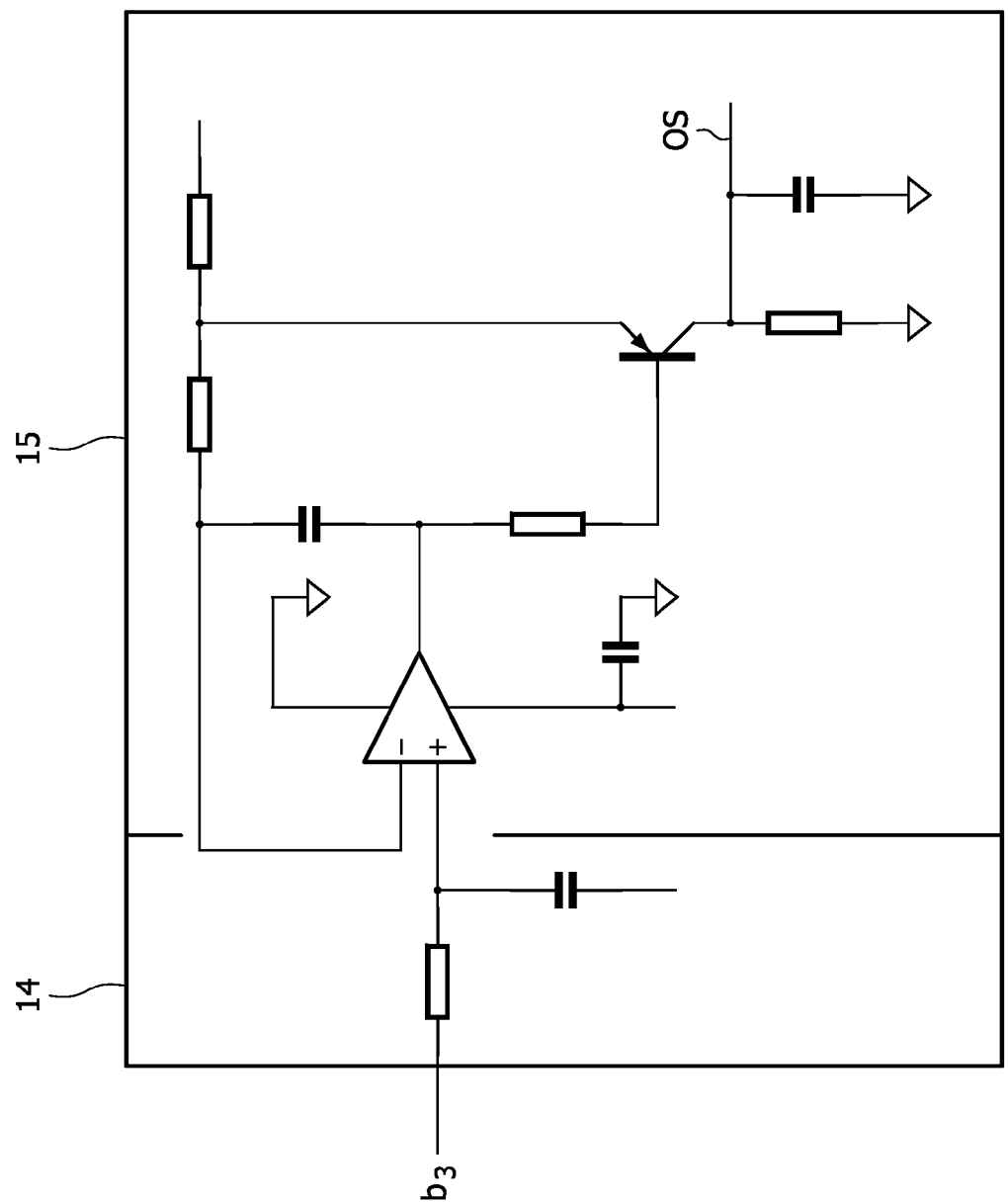

FIG. 2 shows functional block-diagram of the capacitive proximity device 30 comprising an active noise suppression circuit 80 according to the invention. The inventors have found that the known capacitive proximity devices may not function well when applied at the rim of the display device 34 and may be unreliable. The reason for this unreliable capacitive proximity device 30 is that the display of the display device 34 also generates an electric field (see dashed arrows in FIG. 4 originating from the display device 34 towards the receiver electrode RA). To be able to implement the capacitive proximity device 30 at the rim of the display device 34, active noise suppression is required.

The sensing circuit 72 comprises an in measured-signal amplifier 1 arranged in series with a first band-pass amplifier 2, This amplified measured-signal MS is subsequently provided to a first differential amplifier 4 and a second differential amplifier 5, The first differential amplifier 4 is already part of the noise-suppression means 80 and is used to generate a noise-signal NS which represents the noise which is present in the measured-signal MS. The noise-signal NS generated by the noise-suppression means 80 is provided to the inverting input of the second differential amplifier 5 to subtract the noise from the measured-signal to produce a noise-reduced measured-signal NR-MS, A second band-pass amplifier 8 is used before offering the noise-reduced measured-signal NR-MS to the first synchronous detection circuit 13 together with the first low-pass filter 14 to generate the output-signal OS. The sensing circuit 72 further comprises an amplifier 15 before providing the output-signal OS to a microcontroller 16 for evaluating the output-signal.

The noise-suppression means 80 comprises a variable gain amplifier 3, a second synchronous detection circuit 9 together with a second low-pass filter 10, and an integrator circuit 12.

The second synchronous detection circuit 9 together with the second low-pass filter 10 receives the noise-signal NS for generating an effective amplitude EA of the measured-signal MS. The integrator circuit 12 receives the effective amplitude EA and compares the effective amplitude EA with a reference level (for example, ground) for generating a gain-signal GS being provided to the variable gain amplifier 3 and defining a gain of the variable gain amplifier 3. The variable gain amplifier 3 receives the emission-signal ES and the gain-signal GS and adapts the amplitude of the emission-signal ES in accordance with the gain-signal GS to generate the correction-signal CS. This correction signal CS is associated with the measured-signal MS in that the correction-signal CS is a substantially noise-free copy of the sensed-emission-signal SES. The correction-signal CS is subsequently used to generate the noise-signal NS by subtracting the correction-signal CS from the measured-signal MS. A comparator 6 converts the emission signal ES from the oscillator 17 to a reference-signal RS which is provided to a switch control of the first and second synchronous detection circuits 9, 13 that toggles between the signal and its inverse at the zero crossings.

An alternative way of noise suppression is also shown in FIG. 2 in that the 'noise free copy' of the measured-signal MS, being the correction-signal CS at the output of the variable gain amplifier 3 is used as input of the first synchronous detection circuit 13, instead of the output of the second differential amplifier 5. This is indicated in FIG. 2 with the dashed arrow 77 going from the output of the variable gain amplifier 3 to the input of the second band-pass amplifier 8. This alternative embodiment of active noise suppression requires fewer components as it typically requires one less differential amplifier (the second differential amplifier 5). The second band-pass amplifier 8 may still be present, although the band-pass filter may be omitted to further reduce cost.

FIG. 3 shows an actual schematic for the capacitive proximity device 30 comprising active noise suppression circuit 80. The reference numbers shown in FIG. 3 correspond to the reference numbers as shown in FIG. 2. In the boxes of FIG. 3 indicated with the corresponding reference numbers, an actual electronic circuit performing the specific function as explained in relation to FIG. 2 is shown. The skilled person may directly and unambiguously determine the electronic circuit relating to the functional blocks as shown in FIG. 2 from the examples shown in FIG. 3.

Figure 4:
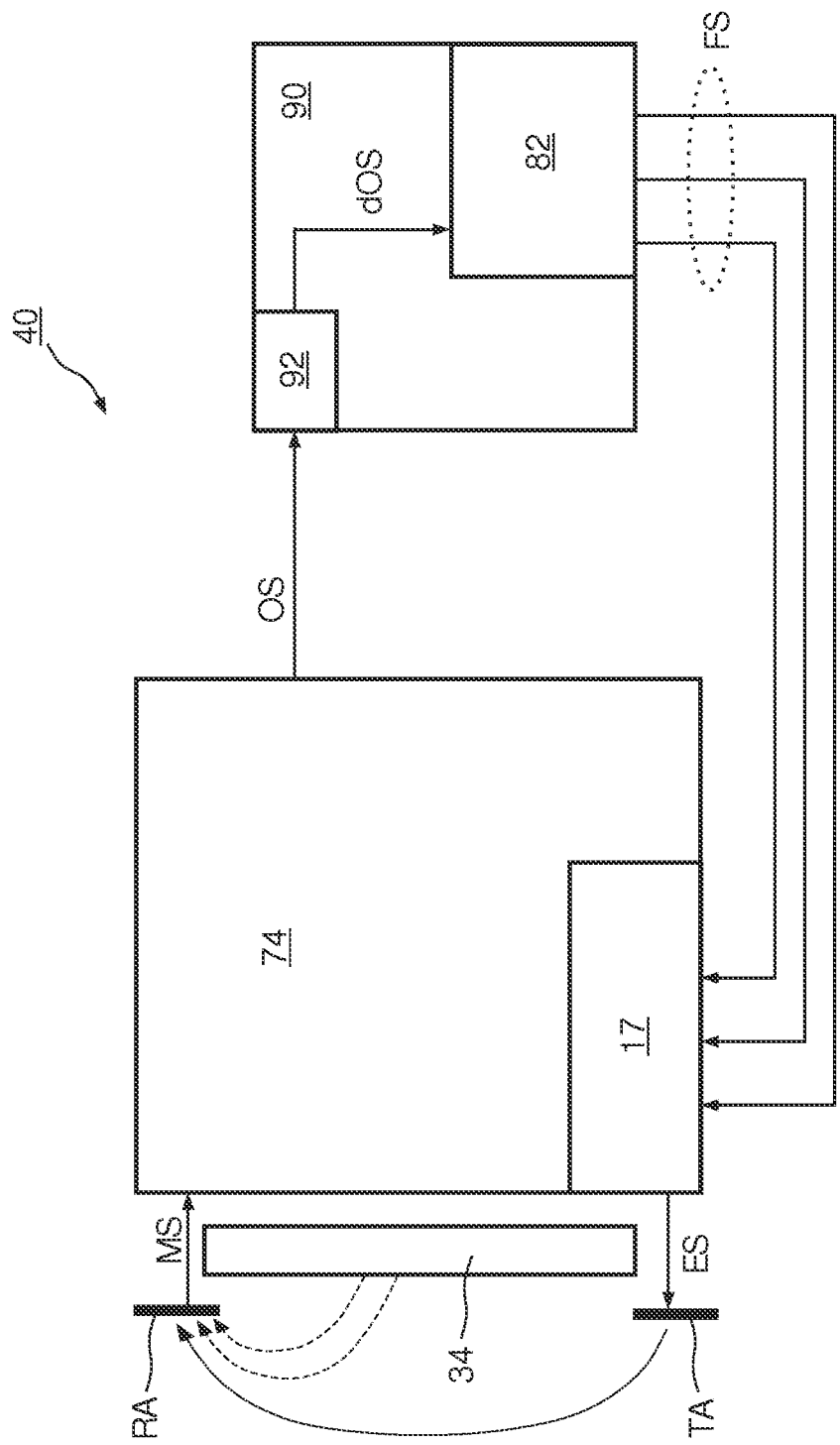
FIG. 4 shows a schematic representation of a capacitive proximity device comprising a beat-detector.

FIG. 4 shows a schematic representation of a capacitive proximity device 40 comprising a beat-detector 82. The schematic representation of FIG. 4 again shows the emission electrode TA and the receiver electrode RA and the display device 34. Furthermore, the sensing circuit 74 is not further specified, but may any of the sensing circuits 74 shown in FIGS. 2, 5 and 6. Still schematically indicated in FIG. 4 is the oscillator 17 being part of the sensing circuit 74. However, the oscillator 17 may be a separate unit from the sensing circuit 17 as indicated in FIGS. 1 and 2. The output-signal OS is provided to a further controller circuit 90, for example, a microcontroller 90 having an analog-to-digital converter 92 for converting the output-signal OS into a digital signal. This microcontroller 90 comprises the beat-detector 82, which in the current example, is built from instructions, instructing the microcontroller 90 to perform the following steps:

receiving the digitized output-signal dOS which is indicative of the distance between the object 32 and the capacitive proximity device 40, analyzing the digitized output-signal dOS for detecting a regular and/or periodic distance variation of the object 32 with respect to the capacitive proximity device 40, the regular and/or periodic distance variation being indicative for a regular and/or periodic signal component in the measured-signal MS, if such regular and/or periodic distance variation is identified: send a frequency-signal FS to the oscillator 17 for altering the frequency of the emission-signal ES.

The frequency and amplitude of the regular and/or periodic signal component in the measured-signal MS which is also indicated as beating are relatively unpredictable and are dependent on the particular display device and the frequency of the oscillator 17. Moreover, the variations are relatively large between oscillators 17 and thus it seems substantially impossible to design the right frequency of the oscillator 17 where no beating occurs. It is however possible to detect the regular and/or periodic signal component, and switch to another oscillator frequency to prevent interference of the output-signal OS.

An example to detect the presence of the regular and/or periodic signal component consist of the following algorithm, which comprises two parts:

A first part checks the number of crossings of an averaged-signal being an average of the measured-signal MS. At any moment in time, the average may be monitored. If the measured-signal MS comprises a regular and/or periodic signal component recognized as beating, than the measured-signal MS at some instances is smaller than the averaged signal, and at other instances larger than the averaged-signal. During a calibration, the number of times measured-signal crosses the averaged-signal is counted, generating a value being proportional to the beating frequency. If there is no beating, and the measured-signal MS is relatively noisy, and thus the measured-signal MS will cross the averaged-signal many times. The number of crossings of the measured-signal MS over the averaged-signal gives us a first indication of the presence of the regular and/or periodic signal component being beating: when the number of crossings is relatively large, then there is no beating, when the number of crossing is relatively small, that the beating may be present.

A second part of the algorithm monitors continuously the standard deviation of the averaged-signal. We are interested, during the calibration, in a signal which is substantially constant. The beating however, destroys this substantially constant averaged-signal, creating oscillations in the averaged-signal. The standard deviation of the averaged-signal gives us a second number: if this second number is relatively small we do not have beating, if this second number is relatively large, we have beating.

The ratio of the two numbers (the standard deviation and the number of the crossings of the measured-signal MS across the averaged signal) gives us a good estimate of the presence of the beating. If this ratio is relatively large, we have probably beating.

Clearly many different algorithms may be defined to detect regular and/or periodic signal component and identify these components as beating, without departing from the scope of the invention.

Alternatively, the beat-detector 82 may be produced in hardware which comprises means for performing above listed method steps.

Figure 5:
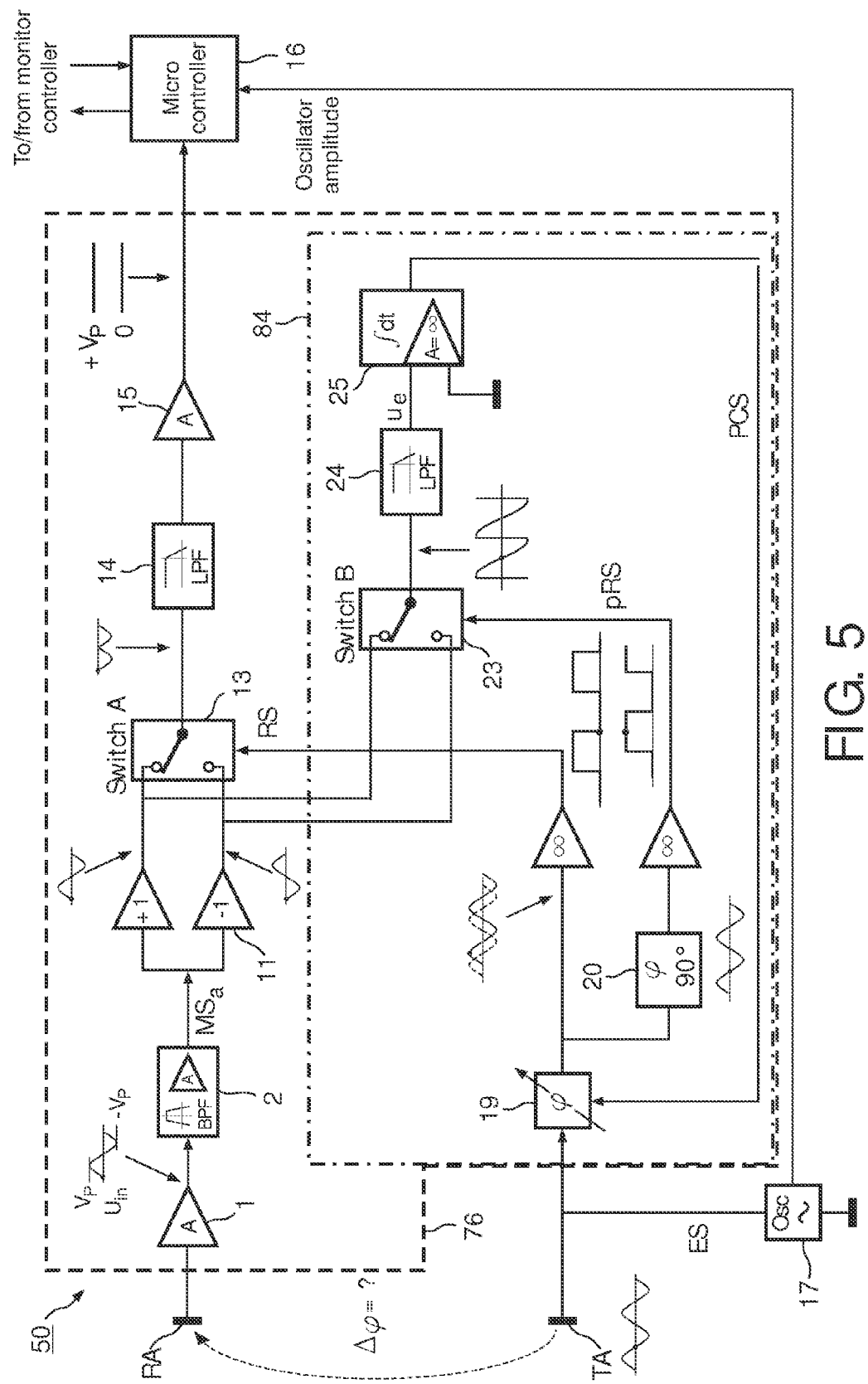
FIG. 5 shows a functional block-diagram of a capacitive proximity device comprising a phase-control circuit.

FIG. 5 shows a functional block-diagram of a capacitive proximity device 50 comprising a phase-control circuit 84. The phase-control circuit 84 comprises a variable phase-controller 19, a third synchronous detection circuit 23 together with a third low-pass filter 24, and a second integrator circuit 25. The third synchronous detection circuit 23 together with the third low-pass filter 24 receives the measured-signal MS and detects the measured-signal MS using a phase-shifted reference-signal pRS being 90 degrees shifted in phase with respect to the reference-signal RS. The second integrator circuit 25 compares the output of the third low-pass filter 23 with a reference level, for example, ground for generating a phase-control-signal PCS which is subsequently provided to the variable phase-controller 19 and defines a phase of the reference-signal RS.

This closed loop phase-control circuit 84 of the reference-signal RS compensates automatically any phase shift in the signal path between the oscillator 17 and the total sensing circuit 76. Several signals are given in the block diagram to ease the reading of the circuit.

Figure 6:
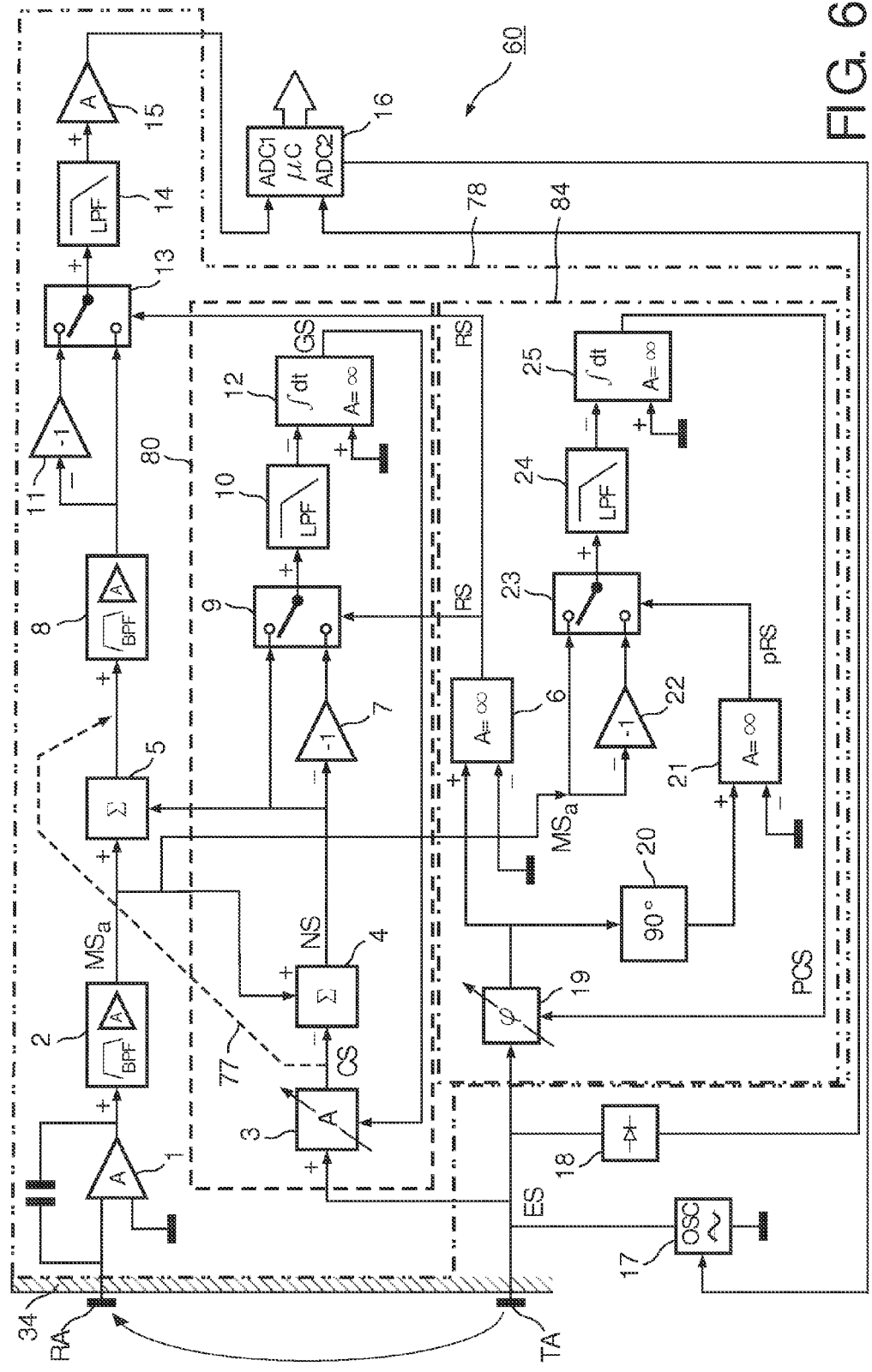
FIG. 6 shows a functional block-diagram in which both the active noise suppression circuit and the phase-control circuit are applied in the capacitive proximity device according to the invention.

FIG. 6 shows a functional block-diagram in which both the active noise suppression circuit 80 and the phase-control circuit 84 are applied in the capacitive proximity device 60 according to the invention. The active noise-suppression circuit 80 is substantially identical to the noise-suppression circuit 80 shown in FIGS. 2 and 3. The phase-control circuit 84 is substantially identical to the phase-circuit 84 shown in FIG. 5. The microcontroller 16 may further comprise the beat-detector 82 (not shown in FIG. 6) for adapting the frequency of the emission-signal ES generated by the oscillator 17 to prevent the regular and/or periodic signal component in the measured-signal MS which is also indicated as beating.

The embodiment shown in FIG. 6 provides the active noise suppression circuit 80 to actively reduce the noise level of the measured-signal MS, and provides the phase-control circuit 84 which ensures that the frequency of the first and second synchronous detection circuits 9, 13 are triggered at the right frequency and phase such that the signal received from the synchronous detection circuits 9, 13 are maximum. This would provide a very reliable capacitive proximity device 60 which beneficially may be used to detect the presence and/or absence of the object 32 or person 32 in front of the display device 34.

FIG. 7 shows the first proximity reference level RL1 and the second proximity reference level RL2. As indicated before, a first comparator 26 (see FIG. 1) is arranged for comparing the output-signal OS level with the first proximity reference-level RL1. When the distance between the object 32 and/or person 32 and the capacitive proximity device 30 decreases, the signal strength of the output-signal OS is reduced (indicated with an arrow having reference number 100). As a consequence, when the signal strength of the output-signal OS is below the first proximity reference-level RL1, the capacitive proximity device 30 considers that the person 32 is close to the display device 34 and thus switches on the display device 34. When the person moves away from the capacitive proximity device 30, the signal strength of the output-signal OS increases again (indicated with an arrow having reference number 102). When the signal strength of the output-signal OS is above the first proximity reference level, the capacitive proximity device 30 considers that the person has left the display device 34 and thus the capacitive proximity device 30 signals the display device 34 to go into the energy reduction mode.

The capacitive proximity device 30 according to the invention also has the second proximity reference level RL2 which is substantially above the "infinity-signal level". This second proximity reference level RL2 is used to indicate a situation in which the object 32 or person 32 is very close to the capacitive proximity device 30, for example, 20 millimeter or less. When the person 32 approaches very close to the capacitive proximity device 30, the person 32 starts to be part of the capacitive proximity device 30 and increases the capacitive coupling between the emission electrode TA and the receiver electrode RA considerably. In such a situation, the output-signal OS typically quickly changes from below the first proximity reference-level RF1 to above the second proximity reference-level RF2 (indicated in FIG. 7 with an arrow having reference number 104), exceeding the "infinity-signal level". This may, for example, occur when the person 32 wants to adapt settings of a display device 30 and has to operate switches at the outer surface of the display device 34, for example at the rim of the display device 34. When such high output-signal OS is detected, the display device 34 must remain switched on and should not start an energy reduction mode to ensure that the person 32 may, for example, see the adaptations he is performing.

Of course, the above mentioned examples all relate to the capacitive proximity devices 30, 40, 50, 60 may be applied at a display device 34. However, it will be directly and unambiguously apparent to the skilled person that the capacitive proximity device 30, 40, 50, 60 may be applied in numerous other electronic devices 34 in which reliable information regarding the distance between the electronic devices 34 and the person 32 is required.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage

The invention claimed is:

1. A capacitive proximity device for sensing a presence and/or absence of an object in proximity of an electronic device, the capacitive proximity device comprising:
    an emission electrode capacitively coupled to a receiver electrode;
    an oscillator configured to generate an emission-signal being an alternating electric field between the emission electrode and the receiver electrode; and
    a sensing circuit connected to the receiver electrode, the sensing circuit receiving a measured-signal from the receiver electrode, and comprising a detection circuit configured to generate an output-signal being proportional to a distance between the object and the electronic device, the measured-signal comprising noise, and the sensing circuit further comprising a noise-suppressor configured to reduce noise from the measured-signal before entering the detection circuit,
    wherein the noise-suppressor comprises a first differential amplifier configured to generate a noise-signal comprising at least a part of the noise from the measured-signal by subtracting a correction-signal from the measured-signal, the correction-signal having substantially a same frequency and phase as the emission-signal and having an amplitude proportional to a sensed-emission-signal.

2. The capacitive proximity device as claimed in claim 1, further comprising a further receiver electrode shielded from the emission-signal for sensing a noise-signal comprising at least a part of noise resulting from the electronic device.

3. The capacitive proximity device as claimed in claim 1, wherein the noise suppressor further comprises a variable gain amplifier, a further detection circuit being a synchronous detection circuit together with a low-pass filter, and an integrator circuit, the synchronous detection circuit together with the low-pass filter receiving the noise-signal for generating an effective amplitude of the sensed-emissionsignal, the integrator circuit receiving the effective amplitude and comparing the effective amplitude with a reference level far generating a gain-signal being provided to the variable gain amplifier and defining a gain of the variable gain amplifier, the variable gain amplifier receiving the emission-signal and the gain-signal and adapting the amplitude or the emission-singal in accordance with the gain-signal to generate the correction-signal.

4. The capacitive proximity device as claimed in claim 1, wherein the noise-suppressor further comprises a second differential amplifier for generating a noise-reduced measured-signal subsequently provided to the detection circuit for generating the output-signal, the second it differential amplifier generating the noise-reduced measured-signal by subtracting the noise signal from the measured-signal.

5. The capacitive proximity devise as claimed in claim 1, wherein the correction-signal is provided to the detection circuit for generating the output-signal.

6. The capacitive proximity device as claimed in claim 1, wherein the noise-suppressor further comprises a beat-detector configured to analyze the measured-signal and/or the output-signal to identify a regular and/or periodic signal component other than a frequency of the emission-signal in the measured-signal.

7. The capacitive proximity device as claimed in claim 6, wherein the beat-detector comprises:
    means for receiving the measured-signal and/or output-signal being indicative of a distance between the object and the capacitive proximity device;
    means for analyzing the measured-signal and/or output-signal detecting a regular and/or periodic distance variation of the object with respect to the capacitive proximity device, the regular and/or periodic distance variation being indicative for the regular and/or periodic signal component in the sensed-emission-signal;
    if such regular and/or periodic distance variation is identified; the capacitive proximity device comprises means for sending a frequency-signal to the oscillator for altering the frequency of the emission-signal.

8. The capacitive proximity device as claimed in claim 7, wherein the oscillator is arranged to switch to a predefined range of frequencies around a center frequency.

9. The capacitive proximity device as claimed in claim 1, wherein the capacitive proximity device further comprises a phase-control circuit for minimizing a phase difference between a reference-signal and the sensed-emission-signal, the reference-signal being used for triggering the detection circuit being a synchronous detection circuit.

10. The capacitive proximity as claimed claim 9, wherein in the phase-control circuit comprises a variable phase-controller, a further synchronous detection circuit together with a low-pass filter, and an integrator circuit, the further synchronous detection circuit together with the low-pass filter receiving the measured-signal and detecting the measured signal using a phase-shifted reference-signal being 90 degrees shifted in phase with respect to the reference-signal, the integrator circuit comparing the output of the low-pass filter with a reference level for generating a phase-control-signal being provided to the variable phase-controller and defining a phase of the reference-signal.

11. The capacitive proximity device as claimed in claim 9, wherein the emission-signal comprises the reference signal.

12. The capacitive proximity device as claimed in claim 1, further comprising:
    a first comparator for comparing the output-signal to a first proximity reference-level for determining the presence and/or absence of the object; and
    a second comparator for comparing the output-signal to a second proximity reference-level for determining the presence and/or absence of the object at close range.

13. The capacitive proximity device as claimed in claim 1, further comprising a calibrator configured to perform periodic calibration of the capacitive proximity device during an absence of the object for correcting changes in surroundings of the capacitive proximity device.

14. A sensing circuit for a capacitive proximity device, the capacitive proximity device comprising:

an emission electrode capacitively coupled to a receiver electrode; and an oscillator configured to generate an emission-signal being an alternating electric field between the emission electrode and the receiver electrode;

wherein the sensing circuit is connected to the receiver electrode, the sensing circuit receiving a measured-signal from the receiver electrode, wherein the sensing circuit comprises a detection circuit configured to generate an output-signal being proportional to a distance between the object and an electronic device, the measured-signal comprising noise, wherein the sensing circuit further comprises a noise-suppressor configured to reduce noise in the measured-signal before entering the detection circuit, the noise-suppressor comprising a differential amplifier configured to generate a noise-signal comprising at least a part of the noise from the measured-signal, and wherein the noise-suppressor comprises a first differential amplifier configured to generate a noise-signal comprising at least a part of the noise from the measured-signal by subtracting a correction-signal from the measured-signal, the correction-signal having substantially a same frequency and phase as the emission-signal and having an amplitude proportional to a sensed-emission-signal.

* * * * *